United States Patent
Ye et al.

(10) Patent No.: US 10,842,384 B2
(45) Date of Patent: Nov. 24, 2020

(54) THERMOCHROMIC OPTICAL WAVEGUIDE TEMPERATURE SENSORS

(71) Applicants: Jing Yong Ye, San Antonio, TX (US); Corinne Nawn, San Antonio, TX (US)

(72) Inventors: Jing Yong Ye, San Antonio, TX (US); Corinne Nawn, San Antonio, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 321 days.

(21) Appl. No.: 15/869,365

(22) Filed: Jan. 12, 2018

(65) Prior Publication Data
US 2018/0192887 A1     Jul. 12, 2018

Related U.S. Application Data

(60) Provisional application No. 62/445,441, filed on Jan. 12, 2017.

(51) Int. Cl.
| | |
|---|---|
| *G01K 11/00* | (2006.01) |
| *G01K 1/00* | (2006.01) |
| *A61B 5/01* | (2006.01) |
| *G01K 13/00* | (2006.01) |
| *G01K 11/16* | (2006.01) |
| *G01K 11/32* | (2006.01) |
| *A61B 5/00* | (2006.01) |

(52) U.S. Cl.
CPC ............ *A61B 5/015* (2013.01); *A61B 5/0084* (2013.01); *A61B 5/01* (2013.01); *G01K 11/165* (2013.01); *G01K 11/3206* (2013.01); *G01K 13/002* (2013.01); *A61B 5/0075* (2013.01)

(58) Field of Classification Search
USPC .................................................. 374/161, 120
See application file for complete search history.

(56) References Cited

U.S. PATENT DOCUMENTS

| | | | | |
|---|---|---|---|---|
| 4,278,349 | A * | 7/1981 | Sander ................... | G01K 11/12 356/44 |
| 4,749,856 | A * | 6/1988 | Walker ................... | G01K 11/18 250/227.11 |
| 5,547,283 | A * | 8/1996 | Kronberg ............. | B23K 37/006 374/162 |
| 6,019,507 | A * | 2/2000 | Takaki ................... | G01K 11/18 374/161 |

(Continued)

OTHER PUBLICATIONS

V Mishra, N Singh, U Tiwari & P Kapur. (2011). "Fiber grating sensors in medicine: current and emerging applications," Sensors and Actuators A, 167(1): 279-290.

(Continued)

*Primary Examiner* — Mirellys Jagan
(74) *Attorney, Agent, or Firm* — Thomas Horstemeyer, LLP

(57) ABSTRACT

In one embodiment, a temperature sensor includes an optical waveguide having a distal tip and a thermochromic sensing element mounted to the distal tip of the optical waveguide, wherein light transmitted through the optical waveguide to the distal tip is reflected back from the thermochromic sensing element and wherein the reflected light provides an indication of a local temperature at a location of the thermochromic sensing element.

2 Claims, 6 Drawing Sheets

(56) References Cited

U.S. PATENT DOCUMENTS

| | | | |
|---|---|---|---|
| 2007/0132898 A1* | 6/2007 | Anderson | G01K 11/165 349/21 |
| 2007/0189359 A1* | 8/2007 | Chen | B82Y 30/00 374/161 |
| 2017/0191107 A1* | 7/2017 | Martini | G01K 11/12 |

OTHER PUBLICATIONS

JY Lefrant, L Muller et al. (2003) "Temperature measurement in intensive care patients: comparison of urinary bladder, oesophageal, rectal, axillary, and inguinal methods versus pulmonary artery core method," Intensive Care Medicine, 29(3): 414-418.

* cited by examiner

THERMOCHROMIC OPTICAL WAVEGUIDE TEMPERATURE SENSORS

CROSS-REFERENCE TO RELATED APPLICATION

This application claims priority to U.S. Provisional Application Ser. No. 62/445,441, filed Jan. 12, 2017, which is hereby incorporated by reference herein in its entirety.

BACKGROUND

It is often necessary to monitor the core body temperature of an individual undergoing a medical procedure. This temperature is commonly monitored with a temperature sensor that is inserted into the esophagus or the rectum.

There are various temperature sensors that are used in such applications, including thermistors, thermocouples, and optical fiber-based sensors. Unfortunately, thermistors have been known to report inaccurate readings when immersed in liquid due to their electrically active nature. As a consequence, thermistors must be placed within a waterproof housing, which can undesirably increase the size of the temperature sensor. In addition, thermistors and thermocouples typically include magnetic metals. As a result, such temperature sensors cannot be used in cases in which the individual is going to be exposed to strong magnetic fields, such as those generated during magnetic resonance imaging (MRI). Clinically, this translates to patients potentially undergoing an MRI procedure without temperature monitoring or postponing care until they would not need sedation or anesthesia and, therefore, core body temperature monitoring.

One current solution to the above-described issues involves fiber optic temperature sensors that employ fiber Bragg gratings (FBGs) or optical microcavity sensors. While these modalities are electrically inactive and safer in sensitive or magnetic environments where other temperature sensors are not appropriate, the fabrication process required to manufacture such fibers is undesirably expensive.

From the above discussion, it can be appreciated that it would be desirable to have a small, low-cost, electrically-inactive, non-magnetic temperature sensor that can provide accurate pinpoint temperature measurements.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it can be appreciated that it would be desirable to have a small, low-cost, electrically-inactive, non-magnetic temperature sensor that can provide accurate pinpoint temperature measurements. Disclosed herein are examples of such temperature sensors. In some embodiments, a temperature sensor comprises an optical waveguide, such as an optical fiber, configured to deliver light to a temperature sensing element configured for insertion into the body. In some embodiments, the temperature sensing element is a thermochromic sensing element, such as a thermochromic liquid crystal, that changes color in response to changes in temperature. When the light delivered by the optical waveguide is reflected back from the temperature sensing element, the spectra and/or intensity of the light can be detected and correlated with a particular temperature. In cases in which the spectra are used to determine the temperature, the reflected light can be measured with a spectrometer. In cases in which the intensity is used to determine the temperature, the reflected light can be monitored with a light intensity sensor, such as a photodiode. The disclosed temperature sensors are safe for in-human use and can be leveraged to detect temperatures at precise locations with minimally invasive procedures.

In the following disclosure, various specific embodiments are described. It is to be understood that those embodiments are example implementations of the disclosed inventions and that alternative embodiments are possible. All such embodiments are intended to fall within the scope of this disclosure.

Figure 1:
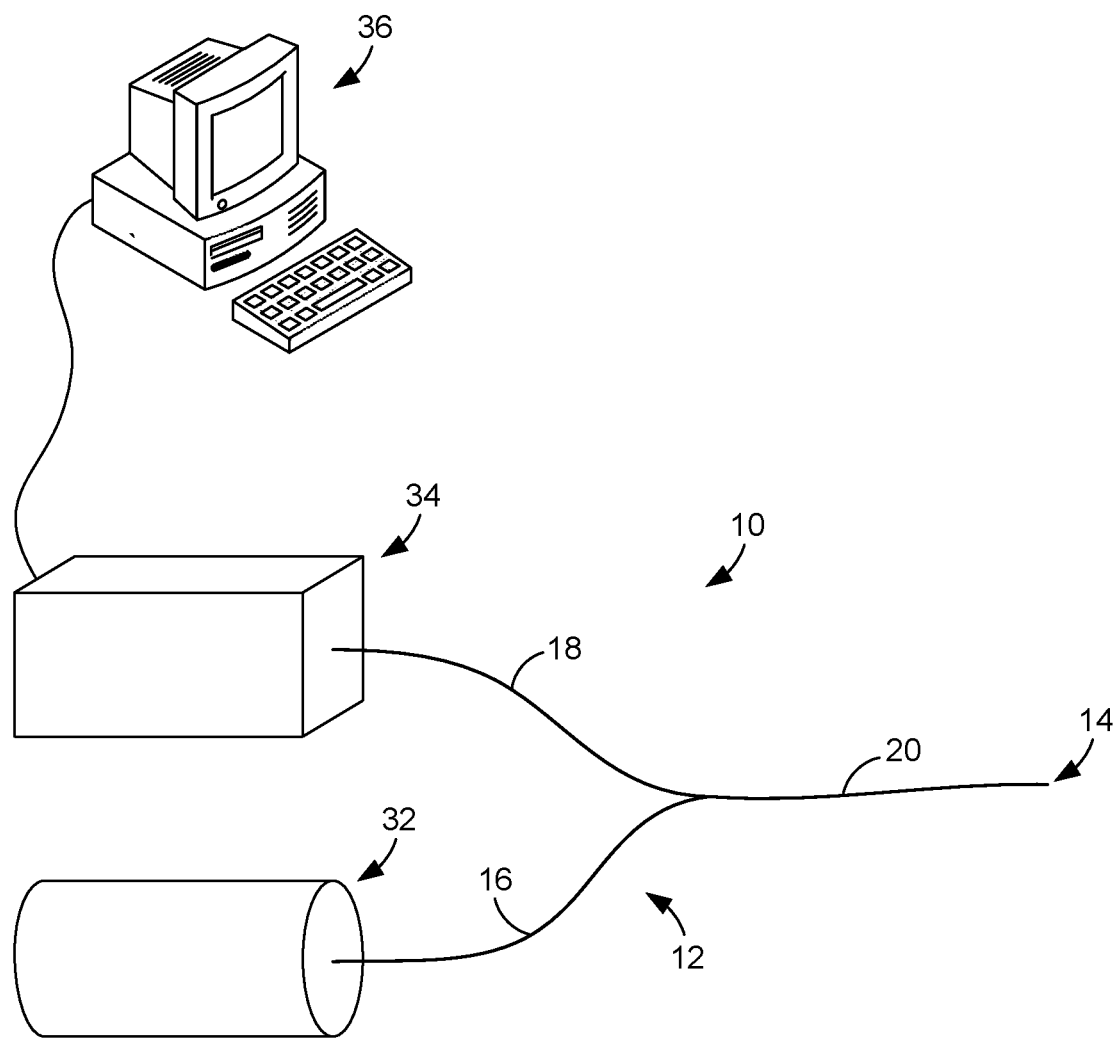
FIG. 1 is a schematic diagram of a first embodiment of a local temperature sensing system.

FIG. 1 illustrates a first embodiment of a temperature sensor 10 that is configured to measure core body temperature. As shown in the figure, the temperature sensor 10 generally comprises an optical waveguide 12, such as an optical fiber, having a temperature sensing element 14 (not visible) provided at a distal tip of the waveguide. In the illustrated embodiment, the optical waveguide 12 includes two proximal optical fiber branches 16 and 18 that are connected to a distal optical fiber branch 20. With such a configuration, light can travel along the first proximal branch 16, through the distal branch 20, and reach the temperature sensing element 14. This light can then reflect off of the temperature sensing element 14, or a reflective element associated with the sensing element, and the reflected light can travel along the distal branch 20 and to the second proximal branch 18 so that the reflected light can be detected and analyzed. While a single optical waveguide 12 that both transmits light to and from the temperature sensing element 14 is shown in FIG. 1, it will be appreciated that two separate optical fibers could be used, one for transmitting light to the sensing element and one for transmitting light from the sensing element.

In some embodiments, the temperature sensing element 14 comprises a thermochromic sensing element, such as a thermochromic liquid crystal, whose color properties change based upon the environmental temperature. As noted above, the temperature sensing element 14 can be mounted to the distal tip of the distal branch 20 of the optical waveguide 12.

Figure 2:
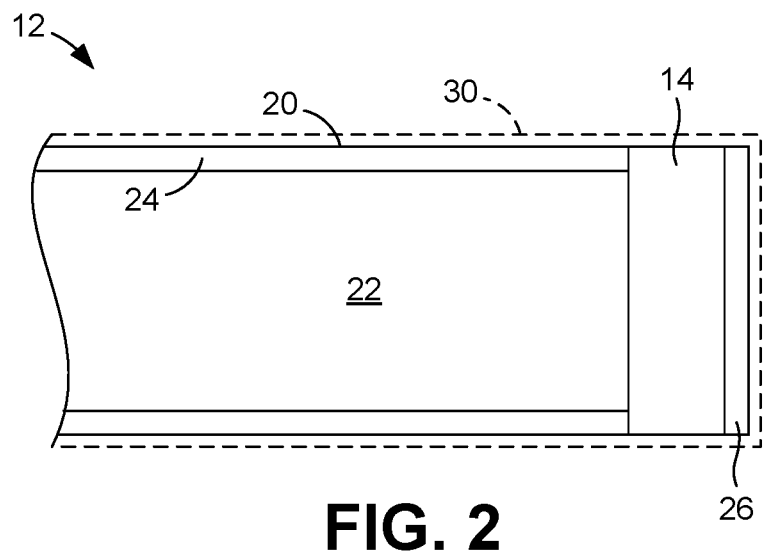
FIG. 2 is a side view of a first example implementation of a temperature sensing element in a temperature sensor shown in FIG. 1.

FIG. 2 illustrates a first embodiment of such mounting. As shown in that figure, the sensing element 14 is directly attached to the distal tip of the distal branch 20 of the optical waveguide 12, which comprises a core 22 that is surrounded by a cladding 24. A reflection element 26 is directly attached to the opposite side of the temperature sensing element 14. In such a case, the light transmitted by the distal branch 20 passes through the temperature sensing element 14, reflects off of the reflection element 26, passes back through the sensing element, and is then delivered back to the distal branch. In some embodiments, the reflection element 26 can comprise a thin non-magnetic, metal (e.g., aluminum) layer or coating.

Figure 3:
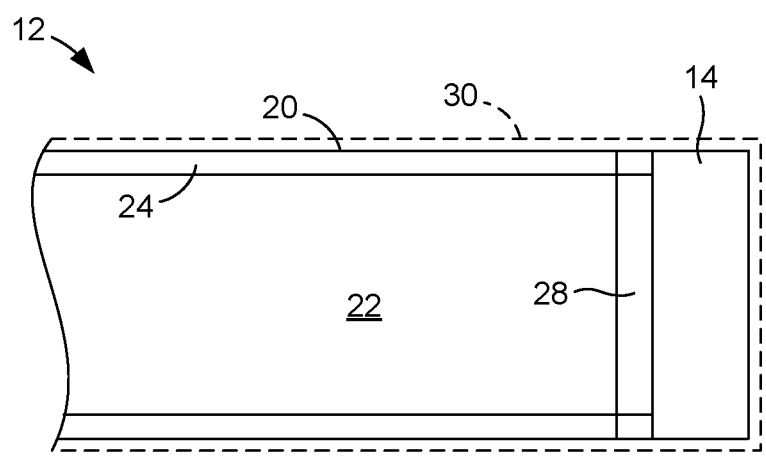
FIG. 3 is a side view of a second example implementation of a temperature sensing element in a temperature sensor shown in FIG. 1.

FIG. 3 illustrates a second temperature sensing element mounting example. In this embodiment, the temperature sensing element 14 is separated from the distal tip of the distal branch 20 by a gap 28. The gap 28 can comprise an air gap or can be occupied by a material having a refractive index that is different from that of the temperature sensing element 14. When the gap 28 is provided, the light emitted onto the sensing element 14 is reflected by the surface of the sensing element back to the distal branch 20. In such a case, the reflection element 26 shown in FIG. 2 is not necessary.

In either of these two alternative embodiments, the distal end of the temperature sensor 10 can be encased or otherwise contained in a protective material. For example, the distal portion of the distal branch 20 that is to be inserted into the body, including the temperature sensing element 14 and the reflection element 26, if provided, can be coated with an inert protective material, such as a polymeric material. Such a coating 30 is depicted in FIGS. 2 and 3 with dashed lines. In other embodiments, the "coating" 30 can be a polymeric outer housing that contains the distal portion of the distal branch 20 and protects it from moisture.

With reference back to FIG. 1, the temperature sensor 10 can comprise part of a temperature sensing system that also includes a light source 32 that delivers light to the optical waveguide 12, a light sensor 34 that receives reflected light from the optical waveguide, and a computer 36 that analyzes the reflected light received by the light sensor. In some embodiments, the light source 32 can comprise a broadband light source and the light sensor 34 can comprise a spectrometer.

The system of FIG. 1 can be used to quantify changes in temperature within a living body, such as a human body, by quantifying the change in color of the temperature sensing element 14. In this embodiment, the reflectance spectra are used to detect the temperature change. During operation of the system, broadband light is coupled into the optical waveguide 12 and delivered to the temperature sensing element 14, which changes its color based upon the local temperature. When this light reflects off of the sensing element 14 or the reflection element 26, the reflected light is transmitted back through the optical waveguide 12 to the spectrometer, which measures the spectra of the back-reflected light. The measured reflectance spectra are analyzed with software (i.e., one or more algorithms comprising logic and executable instructions) that is stored within memory (i.e., a non-transitory computer-readable medium) resident on the computer 36 and the shift of the peak of the reflectance spectrum can be correlated to a particular local temperature. This correlation can be determined from calibrations performed prior to use of the system.

Figure 4:
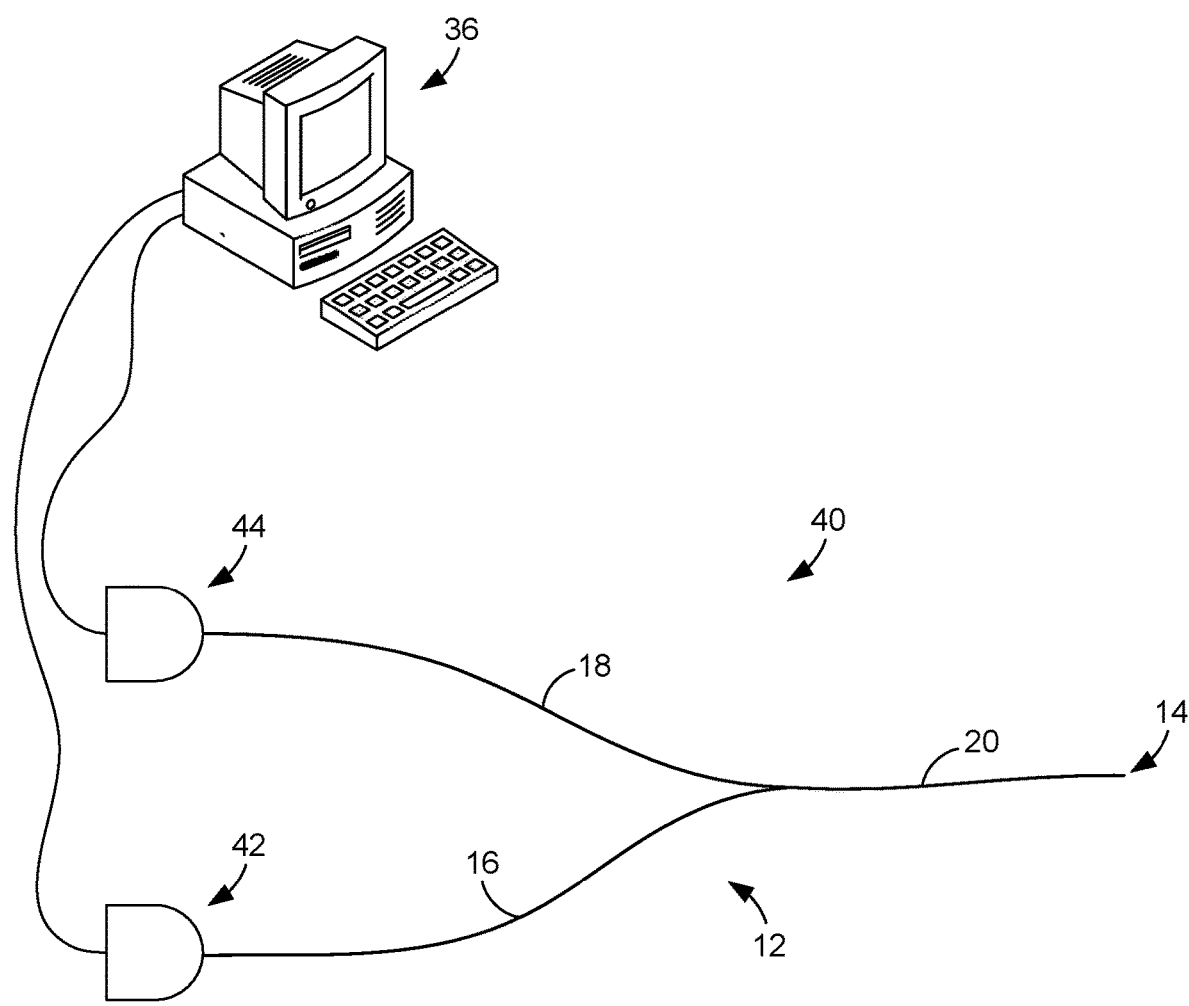
FIG. 4 is a schematic view of a second embodiment of a local temperature sensing system.

FIG. 4 illustrates a second embodiment of a temperature sensing system. The system is similar in many ways to the system shown in FIG. 1. Accordingly, the system uses a temperature sensor 40 that comprises an optical waveguide 12, such as an optical fiber, having two proximal branches 16 and 18 and a distal branch 20 with a temperature sensing element 14 provided at its distal tip. As with the previous embodiment, a reflection element 26 or a gap 28 can be associated with the temperature sensing element 14 in order to reflect light supplied by the first proximal branch 16 back to the second proximal branch 18. In this embodiment, however, a light source 42 having a narrow bandwidth, such as a laser or a color light-emitting diode (LED), is used instead of a broadband light source. In such a case, the intensity of the back reflection of the light from the sensing element 14 is detected with a light sensor 44, which can comprise a photodiode. The differential intensity between the reflected light intensity and the incident light intensity can be calculated by software that executes on the computer 36 (or other logic using discrete components) and used as a parameter to monitor the change in the local temperature.

Figure 5:
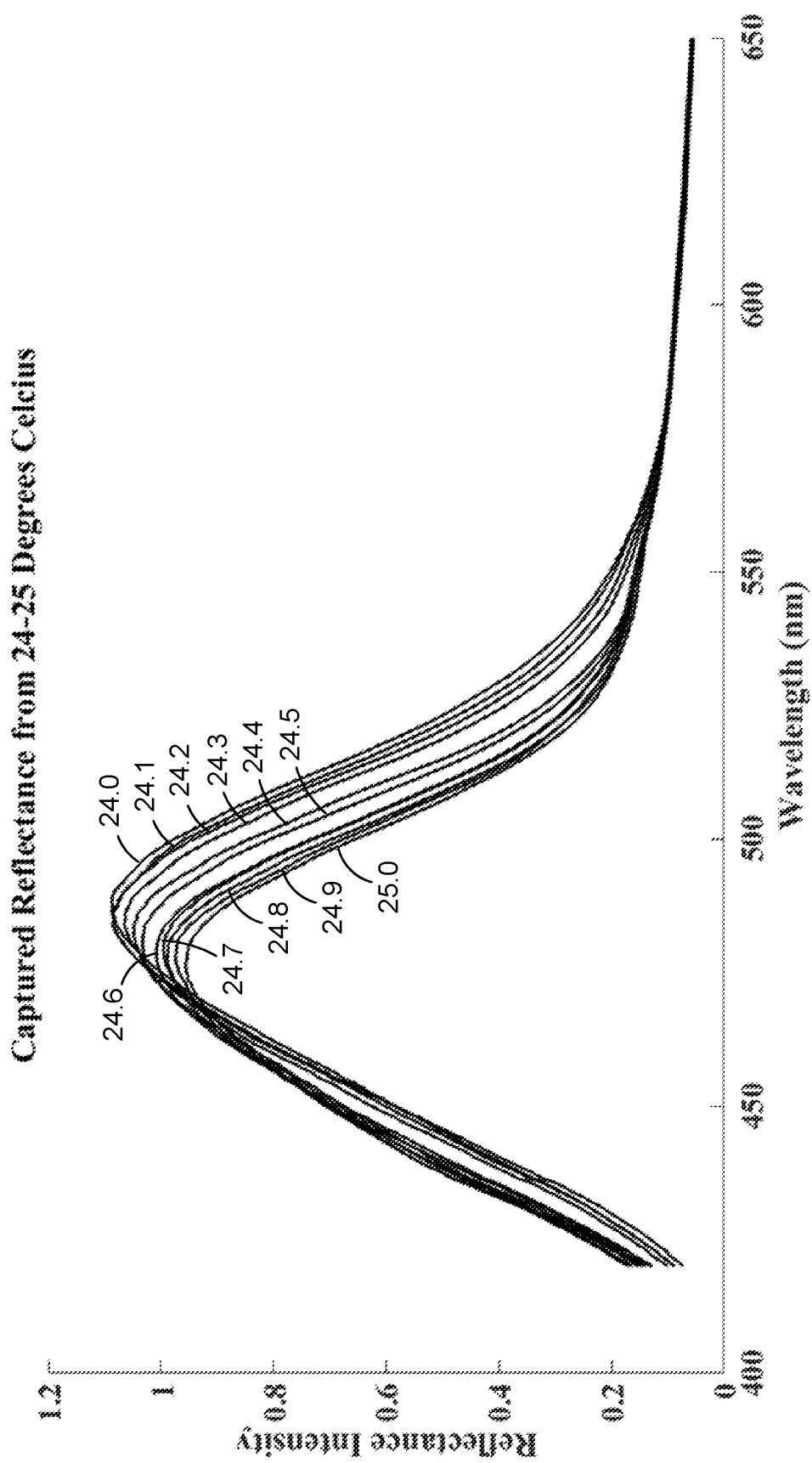
FIG. 5 is a graph that shows the observed shift in the reflectance peak over an interval of 24 to 25° C.

Experiments were performed with temperature sensors and temperature sensing systems similar to those described above. FIG. 5 shows the observed shift in the reflectance peak over an interval of 24 to 25° C. The data was smoothed using a moving average filter.

Figure 6:
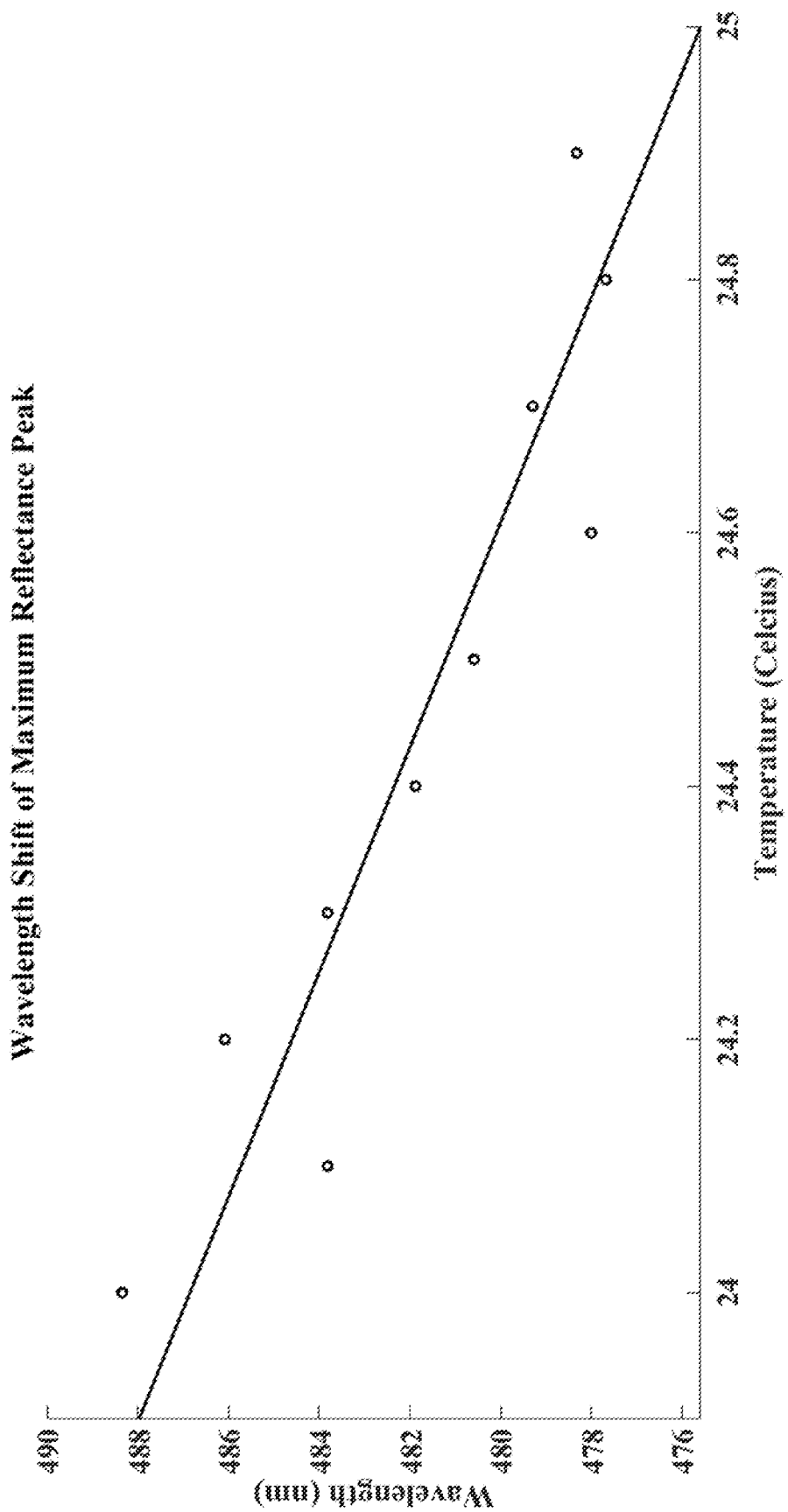
FIG. 6 is a graph that shows a peak wavelength detection as a function of changing temperature.

FIG. 6 shows a scatter plot with a line of least squares for the shift in peak wavelength occurrence to detect the changes in temperature. This method of analysis is one potential implementation of correlating the shift in peak wavelength with the shift in sensed temperature.

Figure 7:
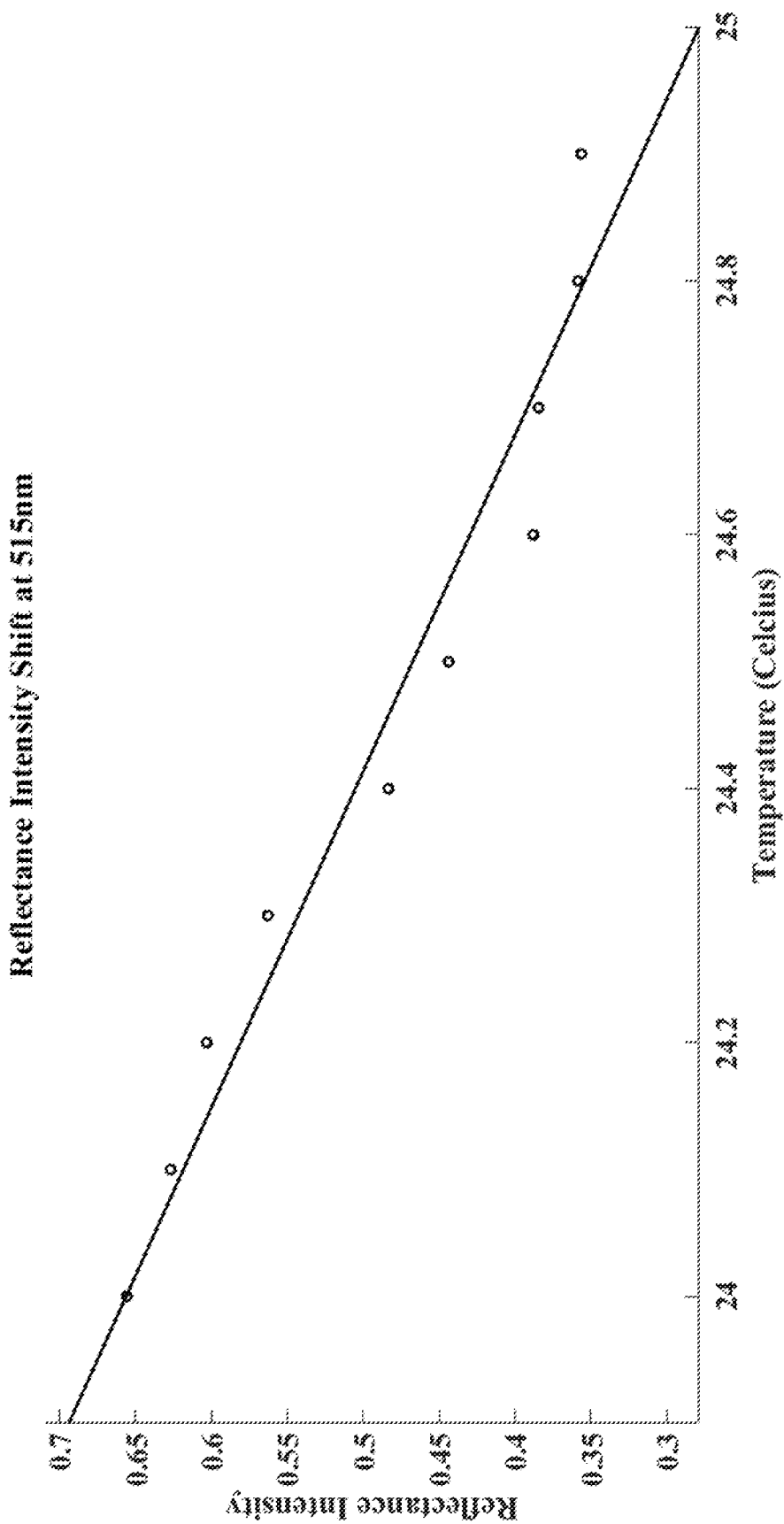
FIG. 7 is a graph that shows a comparison between reflectance intensity of a thermochromic liquid crystal at selected wavelength and the change in temperature.

FIG. 7 shows another potential detection method of quantitatively correlating the shift in the reflectance peak to the shift in temperature by comparing the relative intensity change at a specified wavelength. Using the data shown in FIG. 5, the selected wavelength of 515 nm exhibited a more linear relationship than the peak detection over the 24 to 25° C. range, incrementing by 0.1° C.

Both the peak wavelength detection method and change in relative intensity detection method can be realized using discrete components and filters in accordance with the embodiments of FIGS. 1 and 4.

As noted above, one application for the disclosed temperature sensors is minimally invasive thermometers for pinpoint measurements in vivo. Close monitoring of human core body temperature is crucial for critically ill patients and during operations. The disclosed temperature sensors provide a solution to this clinical problem providing means for reliably monitoring the acute changes in temperature at these deep physiological locations in as minimally invasive a manner as possible. In addition to core body temperature measurement, the disclosed temperature sensors can be used to monitor other pinpoint temperature measurements within or on a body. Examples include quantifying "hot spots" or "cold spots" occurring from local swelling or local heating/cooling. Alternatively, the temperature sensors can be implemented for other physiologic or non-physiologic temperature measurements at pinpoint locations by selecting the temperature sensing element to be sensitized to a desired temperature range.

The invention claimed is:

1. A method of measuring a local temperature, the method comprising:
   delivering light to a thermochromic sensing element with an optical waveguide;
   delivering light reflected by the thermochromic sensing element to a light sensor;
   analyzing the reflected light to identify a change in a peak of reflectance spectra of the reflected light; and
   correlating the identified change to a temperature at the location of the thermochromic sensing element.

2. A method of measuring a local temperature, the method comprising:
   delivering light to a thermochromic sensing element with an optical waveguide;

delivering light reflected by the thermochromic sensing element to a light sensor;

analyzing the reflected light to identify a change in intensity of the reflected light; and correlating the identified change to a temperature at the location of the thermochromic sensing element.

\* \* \* \* \*